(12) United States Patent
Maxwell et al.

(10) Patent No.: US 6,852,212 B2
(45) Date of Patent: Feb. 8, 2005

(54) METHOD AND APPARATUS FOR AUTOMATIC ANALYSIS

(75) Inventors: Ian Andrew Maxwell, Concord (AU); Thomas William Beck, North Richmond (AU); Alastair McIndoe Hodges, San Diego, CA (US)

(73) Assignee: LifeScan, Inc., Milpitas, CA (US)

(*) Notice: Subject to any disclaimer, the term of this patent is extended or adjusted under 35 U.S.C. 154(b) by 0 days.

(21) Appl. No.: 09/970,461

(22) Filed: Oct. 2, 2001

(65) Prior Publication Data

US 2002/0117404 A1 Aug. 29, 2002

Related U.S. Application Data

(63) Continuation of application No. 09/502,907, filed on Feb. 11, 2002, now Pat. No. 6,325,917, which is a continuation of application No. PCT/AU98/00642, filed on Aug. 13, 1998.

(30) Foreign Application Priority Data

Aug. 13, 1997 (AU) .............................................. PO8558

(51) Int. Cl.[7] .................... G01N 27/327; G01N 27/333; G01N 27/28
(52) U.S. Cl. .................... 205/775; 205/777.5; 205/789; 204/403.14; 204/416; 204/400
(58) Field of Search .............................. 205/777.5, 789, 205/775; 204/403.01, 403.14, 403.12, 416, 400

(56) References Cited

U.S. PATENT DOCUMENTS

| | | | |
|---|---|---|---|
| 3,552,928 A | 1/1971 | Fetter | |
| 4,053,381 A | 10/1977 | Hamblen et al. | |
| 4,076,596 A | 2/1978 | Connery et al. | |

(List continued on next page.)

FOREIGN PATENT DOCUMENTS

| | | |
|---|---|---|
| JP | 59-3345 A | 1/1984 |
| JP | 6310746 | 11/1994 |
| AU | A-31042/93 | 7/1993 |
| AU | A-54873/94 | 8/1994 |
| EP | 0 010 457 B1 | 11/1982 |
| EP | 0 251 915 A2 | 1/1988 |
| EP | 0 255 291 A1 | 2/1988 |
| EP | 0 278 647 A2 | 8/1988 |
| EP | 0 345 781 A2 | 12/1989 |
| EP | 0 351 516 A2 | 1/1990 |
| EP | 0 400 918 A1 | 12/1990 |
| EP | 0 407 800 A2 | 1/1991 |
| EP | 0 206 218 B1 | 3/1991 |
| EP | 0 415 679 A2 | 3/1991 |
| EP | 0 418 404 A1 | 3/1991 |
| EP | 0 475 692 A1 | 3/1992 |
| EP | 0 479 394 A2 | 4/1992 |
| EP | 0 560 336 A1 | 9/1993 |
| EP | 0 574 134 A2 | 12/1993 |
| EP | 0 593 096 A2 | 4/1994 |
| EP | 0 127 958 B2 | 4/1996 |
| EP | 0 732 406 A2 | 9/1996 |
| EP | 0 741 186 A2 | 11/1996 |
| EP | 0 764 469 A2 | 3/1997 |
| EP | 0 537 761 B1 | 8/1997 |
| EP | 0 964 059 A2 | 12/1999 |
| GB | 2 201 248 A | 8/1988 |

(List continued on next page.)

*Primary Examiner*—Nam Nguyen
*Assistant Examiner*—Alex Noguerola
(74) *Attorney, Agent, or Firm*—Nutter McClennen & Fish LLP

(57) ABSTRACT

This invention relates to a method for analyzing the concentration of an analyte in a sample and to automatic analyzing apparatus. The invention will be described herein with particular reference to a method and apparatus for measuring the concentration of glucose or other analytes in blood but is not limited to that use.

18 Claims, 3 Drawing Sheets

U.S. PATENT DOCUMENTS

| | | | |
|---|---|---|---|
| 4,125,372 A | 11/1978 | Kawai et al. | |
| 4,168,146 A | 9/1979 | Grubb et al. | |
| 4,224,125 A | 9/1980 | Nakamura et al. | |
| 4,225,557 A | 9/1980 | Hartl et al. | |
| 4,259,165 A | 3/1981 | Miyake | |
| 4,301,412 A | 11/1981 | Hill et al. | |
| 4,301,414 A | 11/1981 | Hill et al. | |
| 4,303,887 A | 12/1981 | Hill et al. | |
| 4,319,969 A | 3/1982 | Oda et al. | |
| 4,374,013 A | 2/1983 | Enfors | |
| 4,404,066 A | 9/1983 | Johnson | |
| 4,431,004 A | 2/1984 | Bessman et al. | |
| 4,431,507 A | 2/1984 | Nankai et al. | |
| 4,508,613 A | 4/1985 | Busta et al. | |
| 4,508,821 A | 4/1985 | Mansour et al. | |
| 4,517,287 A | 5/1985 | Scheibe et al. | |
| 4,517,291 A | 5/1985 | Seago | |
| 4,533,440 A | 8/1985 | Kim | |
| 4,545,382 A | 10/1985 | Higgins et al. | |
| 4,552,840 A | 11/1985 | Riffer | |
| 4,604,264 A | 8/1986 | Rothe et al. | |
| 4,637,978 A | 1/1987 | Dappen | |
| 4,654,197 A | 3/1987 | Lilja et al. | |
| 4,711,245 A | 12/1987 | Higgins et al. | |
| 4,790,979 A | 12/1988 | Terminiello et al. | |
| 4,797,256 A | 1/1989 | Watllington, IV | |
| 4,820,489 A | 4/1989 | Rothe et al. | |
| 4,871,258 A | 10/1989 | Herpichboehm et al. | |
| 4,874,501 A | 10/1989 | Christiansen et al. | |
| 4,883,764 A | 11/1989 | Kloepfer | |
| 4,897,173 A | 1/1990 | Nankai et al. | |
| 4,900,424 A | 2/1990 | Birth et al. | |
| 4,919,770 A | 4/1990 | Preidel et al. | |
| 4,943,522 A | 7/1990 | Eisinger et al. | |
| 4,963,815 A | 10/1990 | Hafeman | |
| 4,988,429 A | 1/1991 | Matthiessen | |
| 4,994,238 A | 2/1991 | Daffern et al. | |
| 5,059,908 A | 10/1991 | Mina | |
| 5,096,809 A | 3/1992 | Chen et al. | |
| 5,120,420 A | 6/1992 | Nankai et al. | |
| 5,122,244 A | 6/1992 | Hoenes et al. | |
| 5,126,034 A | 6/1992 | Carter et al. | |
| 5,128,015 A | 7/1992 | Szuminsky et al. | |
| 5,156,972 A | 10/1992 | Issachar | |
| 5,179,005 A | 1/1993 | Phillips et al. | |
| 5,185,256 A | 2/1993 | Nankai et al. | |
| 5,192,415 A | 3/1993 | Yoshioka et al. | |
| 5,229,282 A | 7/1993 | Yoshioka et al. | |
| 5,264,103 A | 11/1993 | Yoshioka et al. | |
| 5,272,087 A | 12/1993 | El Murr et al. | |
| 5,286,362 A | 2/1994 | Hoenes et al. | |
| 5,288,403 A | 2/1994 | Ohno | |
| 5,288,636 A | 2/1994 | Pollmann et al. | |
| 5,290,420 A | 3/1994 | Matson | |
| 5,306,623 A | 4/1994 | Kiser et al. | |
| 5,312,590 A | 5/1994 | Gunasingham | |
| 5,314,605 A | 5/1994 | Matthiessen | |
| 5,320,732 A | 6/1994 | Nankai et al. | |
| 5,322,610 A | 6/1994 | Ishibashi | |
| 5,348,630 A | 9/1994 | Yagi et al. | |
| 5,382,346 A | 1/1995 | Uenoyama et al. | |
| 5,384,028 A | 1/1995 | Ito | |
| 5,385,846 A | 1/1995 | Kuhn et al. | |
| 5,393,399 A | 2/1995 | Van den Berg et al. | |
| 5,405,511 A | 4/1995 | White et al. | |
| 5,413,690 A | 5/1995 | Kost et al. | |
| 5,418,142 A | 5/1995 | Kiser et al. | |
| 5,437,999 A | 8/1995 | Diebold et al. | |
| 5,508,171 A | 4/1996 | Walling et al. | |
| 5,509,410 A | 4/1996 | Hill et al. | |
| 5,518,590 A | 5/1996 | Fang | |
| 5,520,787 A | 5/1996 | Hanagan et al. | |
| 5,567,302 A | 10/1996 | Song et al. | |
| 5,611,908 A | 3/1997 | Matthiessen et al. | |
| 5,620,579 A | 4/1997 | Genshaw et al. | |
| 5,628,890 A | 5/1997 | Carter et al. | |
| 5,645,709 A | 7/1997 | Birch et al. | |
| 5,863,400 A | 1/1999 | Drummond et al. | |
| 5,942,102 A * | 8/1999 | Hodges et al. | 205/775 |
| 5,965,456 A | 10/1999 | Malmqvist et al. | |
| 5,997,817 A | 12/1999 | Crismore et al. | |
| 6,077,408 A | 6/2000 | Miyamoto et al. | |
| 6,325,917 B1 * | 12/2001 | Maxwell et al. | 205/777.5 |

FOREIGN PATENT DOCUMENTS

| | | | |
|---|---|---|---|
| WO | WO 89/08713 | 9/1989 | |
| WO | WO 92/15701 | 9/1992 | |
| WO | WO 94/02842 | 2/1994 | |
| WO | WO 95/03543 | 2/1995 | |
| WO | WO 95/16198 | 6/1995 | |
| WO | WO 95/21934 | 8/1995 | |
| WO | WO 95/28634 | 10/1995 | |
| WO | 9700441 | * | 1/1997 |
| WO | WO 97/18464 | 5/1997 | |
| WO | WO 97/18465 | 5/1997 | |
| WO | WO 98/11426 | 3/1998 | |
| WO | WO 98/35225 | 8/1998 | |
| WO | WO 98/43073 | 10/1998 | |
| WO | WO 98/43074 | 10/1998 | |
| WO | WO 99/46585 | 9/1999 | |

* cited by examiner

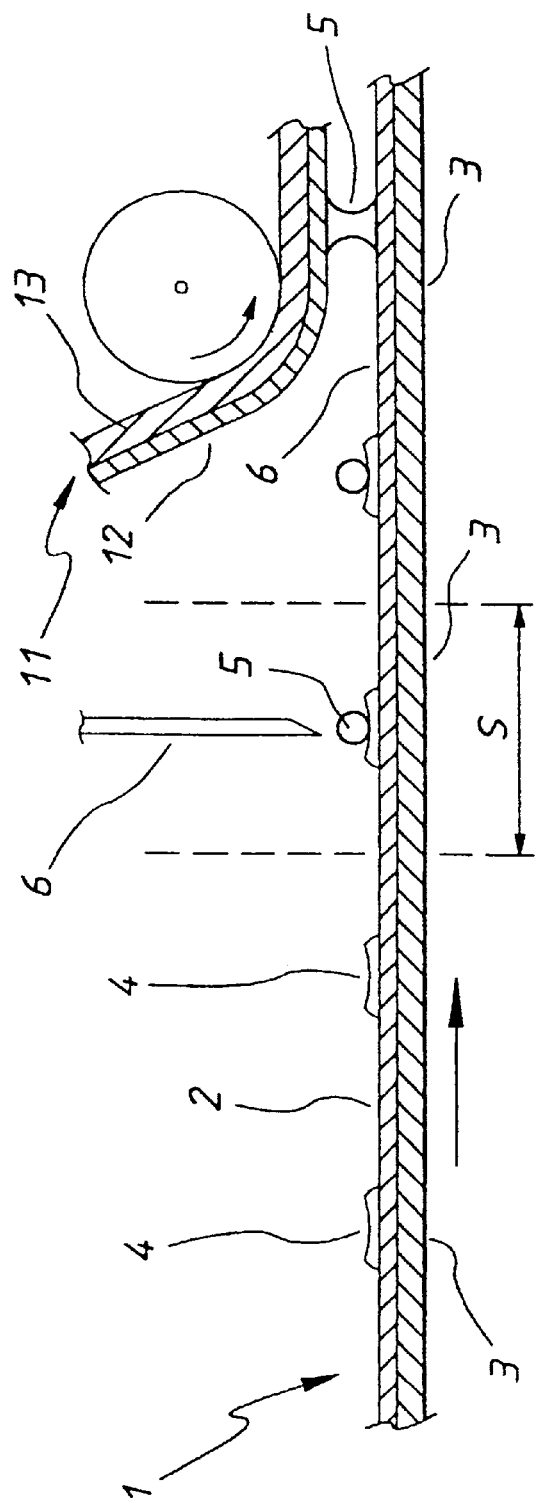
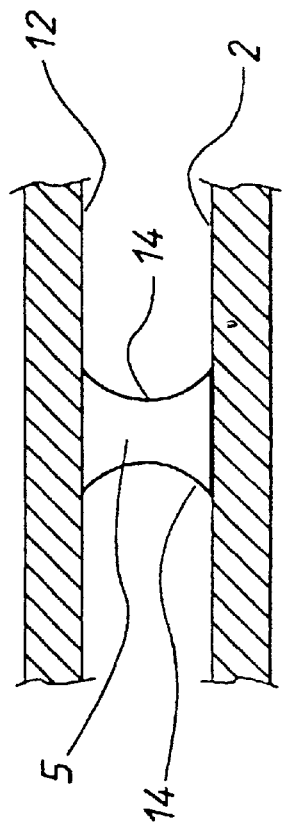

METHOD AND APPARATUS FOR AUTOMATIC ANALYSIS

This application is a continuation of application Ser. No. 09/502,907, filed Feb. 11, 2002 and issued as U.S. Pat. No. 6,325,917 on Dec. 4, 2001, which is a continuation, under 35 U.S.C. §120, of prior PCT International Application No. PCT/AU98/00642 which has an International filing date of Aug. 13, 1998, which designated the United States of America, and which was published by the International Bureau in English on Feb. 25, 1999, and which claims the benefit of Australian Provisional Application No. PO 8558 filed Aug. 13, 1997.

FIELD OF THE INVENTION

This invention relates to a method for analysing the concentration of an analyte in a sample and to automatic analysing apparatus. The invention will be described herein with particular reference to a method and apparatus for measuring the concentration of glucose or other analytes in blood but is not limited to that use.

BACKGROUND ART

In our copending applications PCT/AU/00365, PCT/AU/00723, and PCT/AU/00724 (the disclosures of which are incorporated herein by reference) we have described a method for determining the concentration of an analyte in a carrier. In that method a sample to be analysed is brought into contact with a reagent containing an enzyme and a redox mediator in an electrochemical cell. The cell is a thin layer cell comprising a working electrode spaced apart from a counter electrode by a spacer which ensures that the two electrodes have substantially identical area and predetermined spacing. The spacing between the electrodes is essentially close so that after a potential is applied between the electrodes, reaction products from the counter electrode migrate to the working electrode and vice versa, eventually establishing a steady state concentration profile between the electrodes which in turn results in a steady state current.

It has been found that by comparing a measure of the steady state current with the time rate at which the current varies in the current transient before the steady state is achieved, the diffusion coefficient of the redox mediator can be measured as well as its concentration. It can be shown that over a restricted time range a plot of $\ln(i/i_{ss}-1)$ vs time (measured in seconds) is linear and has a slope (denoted by S) which is equal to $-4 p^2 D/L$, where "i" is the current at time "t", "$i_{ss}$" is the steady state current, "D" is the diffusion coefficient in $cm^2/sec$, "L" is the distance between the electrodes in cm and "p" is the constant pi, approximately 3.14159. The concentration of reduced mediator present when the potential was applied between the electrodes is given by $-2 p^2 i_{ss}/FALS$, where "F" is Faraday's constant, A is the working electrode area and the other symbols are as given above. As this later formula uses S it includes the measured value of the diffusion coefficient.

Since L and the electrode area are constants for a given cell, measurement of i as a function of time and $i_{ss}$ enable the value of the diffusion coefficient of the redox mediator to be calculated and the concentration of the analyte to be determined. In our copending application PCT/AU/00724 there are described methods suitable for mass production of cells having a substantially constant electrode separation L and electrode area A.

Currently glucose in blood samples is measured in pathology laboratories and the like by means of apparatus such the YSI blood analyser in which successive samples are analysed by means of a hollow cylindrical probe in which is mounted a silver and a platinum electrode. The face of the probe is fitted with a three layer membrane. The middle layer contains an immobilized enzyme which is sandwiched between a cellulose acetate and a polycarbonate membrane. The face of the probe, covered by the membrane, is situated in a buffer filled sample chamber into which successive samples are injected. Some of the sample diffuses through the membrane. When it contacts the immobilised oxidase enzyme it is rapidly oxidised producing hydrogen peroxide, the glucose forming a glucono-delta-lactone.

The hydrogen peroxide is in turn oxidised at the platinum anode producing electrons. A dynamic equilibrium is achieved when the rate of peroxide production and removal reach a steady state. The electron flow is linearly proportioned to the steady state peroxide concentration and therefore to the concentration of the glucose.

The platinum electrode is held at an anodic potential and is capable of oxidising many substances other than hydrogen peroxide. To prevent these reducing agents from contribution to sensor current, the membrane contains an inner layer consisting of a very thin film of cellulose acetate. This film readily passes hydrogen peroxide but excludes chemical compounds with molecular weights above approximately 200. The acetate film also protects the platinum surface from proteins, detergents, and other substances that could foul it. However the cellulose acetate film can be penetrated by compounds such as hydrogen sulphide, low molecular weight mercaptans, hydroxylamines, hydrozines, phenols and analytes.

In use, the sample (or a calibration standard) is dispensed in to the chamber, diluted into 600 microliters of buffer, and then a measurement is made by the probe. The sensor response increases and then reaches a plateau when a steady state is reached. After several seconds a buffer pump flushes the chamber and the sensor response decreases.

The apparatus monitors the base line current. If it is unstable a buffer pump will continue to flush the sample chamber with buffer. When a stable base line is established an automatic calibration is initiated. The apparatus calibrates itself for example after every five samples or 15 minutes. If a difference of more than 2% occurs between the present and previous calibration, the apparatus repeats the calibration. Recalibration also occurs if the sample chamber temperature drifts by more than 1° C.

The apparatus described suffers from a number of disadvantages. Firstly, a high proportion of its time in use is spent in performing calibrations rather than analysis. Furthermore the consumption of buffer and calibrating solutions is a substantial cost. Another disadvantage is that as the enzyme membrane ages, a graph of reading versus concentration becomes non-linear. It would be highly desirable to provide apparatus which is able to make measurements of the kind described with improved speed, efficiency, and at lower running cost.

OBJECT OF THE INVENTION

An object of the present invention is an improved method and apparatus for automatically analysing samples which avoids or ameliorates at least some of the disadvantages of prior art. An object of the preferred embodiment of the invention is an automatic apparatus for estimating the concentration of glucose in samples of blood.

BRIEF DISCLOSURE OF THE INVENTION

According to a first aspect the invention consists in a method for estimating the concentration of a reduced (or oxidised) form of a redox species in a liquid comprising the steps of:

(1) contacting an area of a first electrode with a sample of predetermined volume of the liquid, (2) contacting the sample with an area of a second electrode spaced apart from the first, (3) applying a potential between the electrodes while the electrodes are sufficiently closely spaced that reaction products formed at each electrode diffuse to the other electrode while the potential is applied, (4) measuring or estimating a value indicative of the change in current as a function of time and a value indicative of the steady state current, and (5) determining from said volume, said current as a function of time, and said steady state current, the concentration of reduced (or oxidised) form of the species in the liquid sample.

According to a second aspect the invention consists in automatic analysing apparatus comprising:

a first electrode, means for placing a drop of predetermined volume of a liquid sample in contact with the first electrode, means for contacting the drop with a second electrode spaced from the first, means for applying a potential between the electrodes, and means for measuring the current as a function of time while the electrodes are in sufficiently close proximity that reaction products formed at one electrode diffuse to the other and achieve a steady state distribution.

BRIEF DESCRIPTION OF THE DRAWINGS

Various embodiments of the invention will now be described by way of example only with reference to the accompanying drawings wherein:

FIG. 1 is a schematic diagram showing in cross-section a first embodiment of apparatus according to the invention.

FIG. 2 is a schematic diagram showing, in enlarged cross-section, a sample droplet between two electrodes.

DESCRIPTION OF PREPARED EMBODIMENTS

Figure 3:
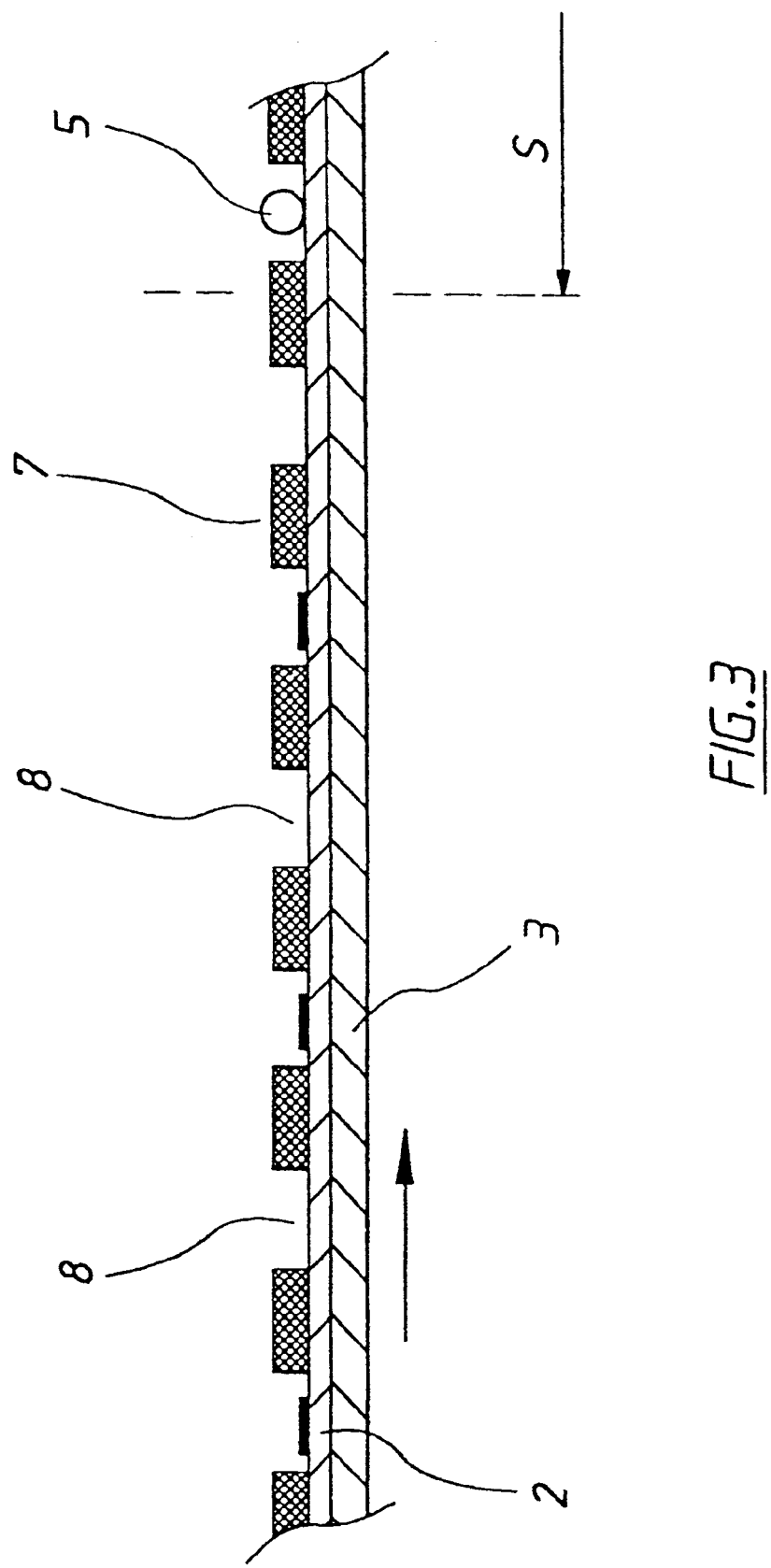
FIG. 3 is a schematic diagram showing in cross-section a second embodiment of apparatus according to the invention.
Figure 5:
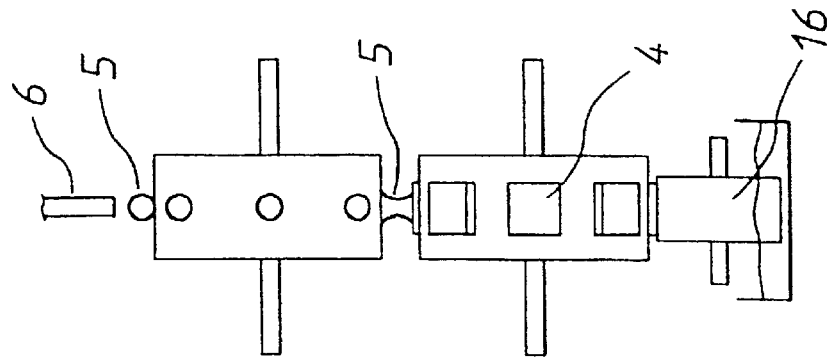
FIG. 5 shows the embodiment of FIG. 4 in end elevation, viewed on line 5—5 of FIG. 4.

By way of example a first embodiment of apparatus according to the invention will be described.

With reference to FIG. 1 there is shown schematically an automatic analyser for measuring glucose in blood samples. The apparatus comprises a flexible first electrode 1 consisting of a palladium layer 2 formed or deposited onto a flexible carrier 3 (for example a 100 micron PET film) preferably by sputter coating to a thickness of for example 100–1000 angstrom. Electrode 1 is fed into the analyser from a roll (not illustrated) in the form of a tape.

First electrode 1 is provided on palladium surface 2 with an enzyme and a redox mediator. These may be selected (without limitation) from the systems in table 1 and in the present example a GOD enzyme and ferricyanide mediator are used. The enzyme and redox mediator may be printed in predetermined quantities at predetermined intervals on the first electrode surface as a dried reagent coating 4.

Electrode 1 is driven by means not shown in the drawings through a sample station "S" at which a precise volume of a sample 1 is placed as a droplet 5 on a reagent coating 4 on electrode surface 1, for example, by means of an automatic pipette 6. Less preferably, predetermined quantities of enzyme and redox mediator may be combined with the sample before or after deposition of the droplet on the electrode.

A second electrode 11 which in the present example is of similar construction to the first electrode, and comprising a palladium layer 12 sputter coated onto a flexible PET carrier 13, is then brought into closely spaced relationship with electrode 1 and into contact with a droplet 5. The droplet wets both palladium surfaces 1 and 10 and adopts a substantially cylindrical configuration between the two electrodes as more clearly illustrated in FIG. 2. The droplet is bounded intermediate electrodes 1, 2 by a liquid/gas interface 14.

An electric potential is then applied to the two electrodes (by means not illustrated in FIG. 1) via contacts.

As described in our co-pending applications PCT/AU96/00723 and PCT/AU96/00724, the potential between the electrodes is set such that the rate of electro-oxidation of the reduced form of the species (or of electro-reduction of the oxidised form) is diffusion controlled. Because the working and counter electrodes are placed in very close proximity (about 0.5 mm apart or less) ferricyanide that is generated at the counter electrode has time to reach the working electrode and contribute to the current at the working electrode. That is, a ferricyanide molecule can be reduced at the counter electrode to ferrocyanide, and can then diffuse to the working electrode, where it will be re-oxidised to ferricyanide. This situation results in a decreasing current at short times that steadies to reach a constant value at longer times (the steady state current). This steadying of the current occurs because a constant stream of ferrocyanide is being supplied to the working electrode from the counter electrode. This mechanism is quite distinct from that which occurs in a Cottrell device in which the electrodes are separated so that ferricyanide that results from the reduction of ferricyanide at the counter electrode does not influence the observed current.

In the present cell the steady state current is given by $$i_{ss} = \frac{2DFAC_0}{L} \tag{1}$$

wherein $i_{ss}$ is the steady state current, D is the diffusion coefficient, F is the Faraday constant, A is the area of the electrode, $C_0$ is the concentration of the analyte (ferricyanide) and L is the separation of the electrodes.

The current i at time t is given by the equation:

$$i = i_{ss}\left(1 + 2\sum_{n=1}^{\infty} e^{\frac{-4p^2n^2Dt}{L^2}}\right) \tag{2}$$

where p is pi.

At longer times the higher exponential terms in equation 2 can be ignored. Therefore equation 2 can be approximated by equation 3 for times greater than a certain value $$i = i_{ss}\left(1 + 2\exp\left(\frac{-4p^2Dt}{L^2}\right)\right) \tag{3}$$

If it is assumed that equation 2 can be approximated by equation 3 when the second exponential term in equation 2 is 1% of the first exponential term, equation 3 is valid for times greater than $$t = \frac{0.0389L^2}{D}.$$

It will be understood that Equation 3 can be transformed to give:

$$\ln\left(\frac{i}{iss} - 1\right) = \ln(2) - 4p^2 \frac{Dt}{L^2} \quad (4')$$

So a plot of the left hand side of equation (4') versus time will give a straight line with new $$slope = -4p^2 \frac{Dt}{L^2} \quad (5')$$

Combining equations (1) and (5') gives $$Co = -\frac{2p^2 iss}{FVslope} \quad (6')$$

where V=AL is the volume of the drop of sample pipetted onto the tape. Since the parameters "slope" and "iss" are measured in the test and p and F are universal constants, to measure the concentration of the analyte derived from the test (Co) it is only required to know the volume of the sample pipetted. Since this can be done very accurately it is possible to have a very accurate measure of Co without the need for any other calibration of the system. Significantly, neither the spacing between the electrodes nor the electrode area wetted need be known.

The exact shape adopted by the droplet in contact with the two electrodes is not important.

If desired the chemistry of successive electrode locations could be different one from another so that a multiplicity of different tests could be performed on successive pipetted volumes of sample placed at successive electrode locations. In a second embodiment as shown in FIG. 3 which corresponds to the portion of FIG. 1 upstream from sample station S, the first electrode is provided with an overlying layer 7 for example of a thin PET film from which apertures have been punched to define wells 8 into which chemical reagents 4 can be placed, and which served to define the locations at which reagents have been placed and/or to protect the reagents prior to use. In this case electrode 1 is conveniently supplied to the apparatus from a roll having predetermined quantities of chemical reagents in the wells in dried form and protected from contamination prior to use by being sandwiched between layers of the roll. The chemical reagents are only used once and therefore can be more easily protected against deterioration than is possible with prior art. In the above described embodiment the sample droplet 5 is not "contained" by a cell although it may be deposited and located within a well 8. When a well-defining layer 7 is employed it may be adhered to the electrode surface or electrode carrier or it may merely be a non-adhered spacer layer.

It is not necessary for the upper electrode layer 11 to come into contact with the top surface of the well-defining layer 7 The volume of sample pipetted is such that the height of drop 5 is equal to or preferably greater than the thickness of the well-defining layer 7. If a layer 7 is used to define a well 8, it is undesirable for the sample volume to run to the sides of the well. It is sufficient that the sample is a known volume and wets both electrodes preferably forming a substantially cylindrical shape therebetween.

It will also be understood that the well-defining layer 7 can be replaced with a porous layer for example a porous paper, non-woven mesh, or felt, or a porous membrane, which acts to immobilise the sample spatially with respect to the electrode layers and to hold the reagents in place and in this case the second electrode will contact the surface of the porous layer immobilising the volume.

It will be understood that use of a porous or well-defining layer 7 is optional and that in other embodiments of the invention a layer 7 is unnecessary it being sufficient for a drop of sample to be pipetted onto a metal layer 2 and for an upper metal layer 12 to be brought into contact with a sample drop of predetermined volume, upper metal layer 12 being desirably but not essentially at a predetermined spacing from the lower metal layer 1.

It will also be understood that the metal layer tapes or bands need not be travelling in the same direction. For example, one metallised electrode layer may be proceeding transversely of the other, each tape being advanced after each measurement to expose a fresh lower and fresh upper electrode surface and fresh reagent at the sample filling station. In each case the resulting current is measured as a function of time while the electrodes are in contact with a sample drop of predetermined volume.

Continuous band electrodes are preferred. These may either be disposed of after use or may be passed through a washing station and then reused, if desired after reprinting with reagents.

In preferred embodiments of the invention predetermined quantities of reagent are placed on one or both of the electrodes by metering devices for example an ink jet print-head upstream of sample station 3 and may, but need not, be dried prior to contact with the sample. A reagent application system may be a part of the apparatus, or the apparatus may be adapted to receive electrodes in roll or other form pretreated with the desired reagents at another location or plant.

Figure 4:
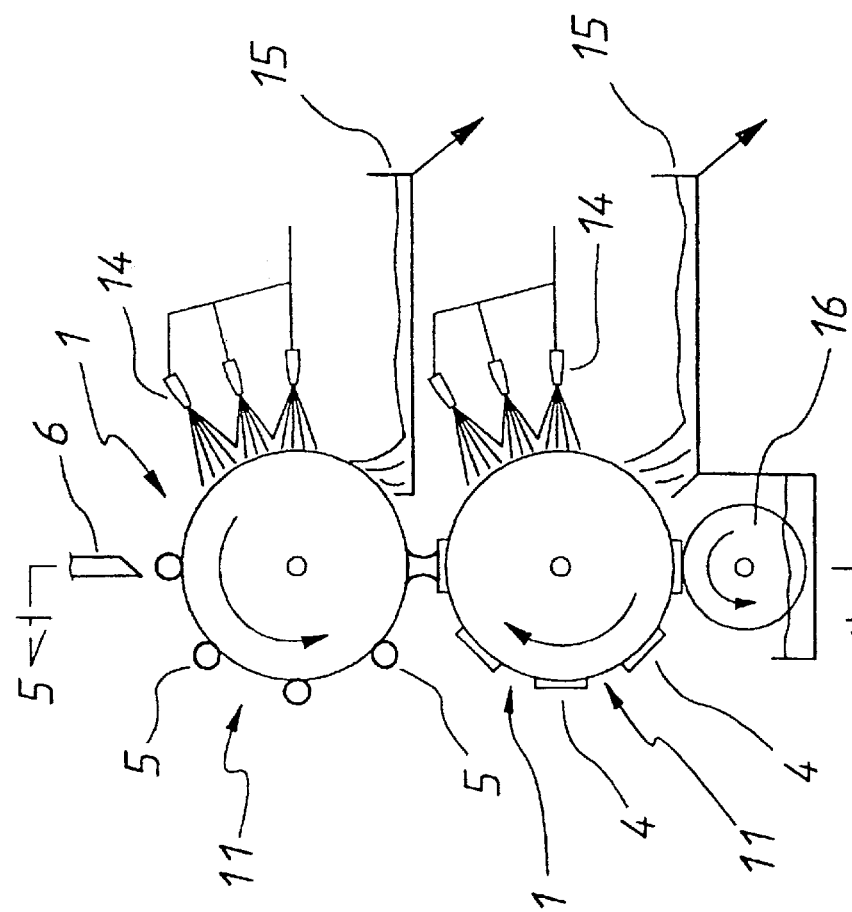
FIG. 4 is a schematic diagram of a third embodiment of apparatus according to the invention in side elevation.

It will be understood that one or both electrodes need not be a continuous band but may, for example, be in the form of a retractable probe. The second electrode could be a disposable probe lowered into contact with a droplet on a first electrode and then withdrawn after current measurements are completed. Likewise the first electrode need not be in the form of a tape. The first electrode could for example be mounted to a carousel or be in the form of a rotating disc. Although it is preferred to use disposable electrode surfaces, the method may be applied with reusable electrodes washed in between successive uses. By way of example, there is shown schematically in FIG. 4 an automatic analysing apparatus comprising a first electrode 1 in the form of a first disc driven intermittently in rotation about a first horizontal axis. A second electrode 11 is driven intermittently and synchronously with the first disc in rotation about a horizontal axis parallel to the first axis. Electrodes 1 and 11 are spaced apart at their edge at the closest point of approach. Sample drops 5 of precisely predetermined volume are deposited on the first electrode at intervals by a pipetting device 6 in synchronisation with the disc rotation. Reagents 4 are printed on the second electrode at corresponding intervals by means of a printing roll 16 and are dried in situ, for example by an air blower (not shown in the drawing).

In use, as electrode 1 rotates, a drop 5 travels to a position where it comes into contact with the second electrode and with the reagents printed thereupon. While both discs are stationary with the droplet in contact with each electrode, a potential is applied between the electrodes and the current measured as previously discussed. During this time the reagent(s) dissolve in the sample and after the necessary measurements have been made, both electrodes are indexed to a new angle of rotation. The surfaces used for the analysis are washed clean by sprays 14, into drained sumps 15 and ready for reuse.

Apparatus according to the invention requires very much smaller samples than are required with the YSI device and because the chemical reagents can be better protected until used and more accurately metered, the apparatus provides greater accuracy and speed at reduced cost.

In another embodiment of the invention the current can be followed with time after a potential has been applied between the electrodes until a predetermined time or state has been reached. The sign of the applied potential would then be reversed and analysis performed similar to that given above except with equations (3) and (4) being replaced with $$i = iss\left(1 + 4\exp\left(-4p^2 \frac{Dt}{L^2}\right)\right) \quad (7)$$

$$\ln\left(\frac{i}{iss-1}\right) = \ln(4) - 4p^2 \frac{Dt}{L^2} \quad (8)$$

Although the invention has been described with reference to palladium electrodes, the electrodes can be of other suitable metals such as described for example in our earlier applications referred to herein. One electrode may be different from the other. The electrodes may be supported by PET as exemplified above or by other suitable insulating materials or may be self-supporting. If supported on an insulating film, it is preferred, but not essential, that the metals be deposited on the film by sputter coating. Electrical contact for the application of a potential and/or for the measurement of current may be by any suitable means including clamping engagement with one end of the electrode if in the form of a tape, or by means of suitable rolling contacts, or springloaded contacts, or the like. The application of the electrical potential; the measurement of current; the calculation of the concentration of analyte; the synchronous control of the movement of one electrode with respect to the other and with the deposition of sample droplets and, if required, with the deposition of reagents may be controlled by a microprocessor or the like and the results may be printed, displayed, and/or otherwise recorded by means which are well-known to those skilled in the control arts.

As will be appreciated by those skilled in the art from the teaching hereof the features of one embodiment may be combined with those of another and the invention may be embodied in other forms without departing from the concepts herein disclosed.

TABLE 1

| ANALYTE | ENZYMES | REDOX MEDIATOR (OXIDISED FORM) | ADDITIONAL MEDIATOR |
|---|---|---|---|
| Glucose | GDHpqq | Ferricyanide | |
| Glucose (NAD dependent) | Glucose dehydrogenase and diaphorase | Ferricyanide | |
| Cholesterol | Cholesterol esterase and cholesterol oxidase | Ferricyanide | 2,6-dimethly-1,4-benzoquinone 2,5-dichloro-1,4-benzoquinone or phenazine ethosulfate |
| HDL cholesterol | Cholesterol esterase and cholesterol oxidase | Ferricyanide | 2,6-dimethly-1,4-benzoquinone 2,5-dichloro-1,4-benzoquinone or phenazine ethosulfate |
| Triglycerides | Lipoprotein lipase, glycerol kinase, and glycerol-3-phosphate oxidase | Ferricyanide or phenazine ethosulphate | Phenazine methosulfate |
| Lactate | Lactate oxidase | Ferricyanide | 2,6-dicholoro-1,4-benzoquinone |
| Lactate | Lactate dehydrogenase and diaphorase | Ferricyanide, phenazine ethosulfate, or phenazine methosulfate | |
| Lactate dehydrogenase | Diaphorase | Ferricyanide, phenazine ethosulfate, or phenazine methosulfate | |
| Pyruvate | Pyruvate oxidase | Ferricyanide | |
| Alcohol | Alcohol oxidase | Phenylenediamine | |
| Bilirubin | Bilirubin oxidase | 1-methoxy-phenazine methosulfate | |
| Uric acid | Uricase | Ferricyanide | |

This protocol has the advantage of being able to allow for slow processes occurring in the test. This can be done by:

a) waiting for the current to change by less than a predetermined amount per second before reversing the potential, such that any slow processes which effect the measurement are substantially complete, or b) using the change in the current with time before the potential is reversed to compensate for the slow processes occurring (as has been described in our earlier patent applications in relation to cells having a predefined electrode separation and area).

What is claimed is:

1. A method for estimating the concentration of a reduced or oxidized form of a redox species in a liquid comprising the steps of:
   (1) contacting an area of a first electrode with a sample of predetermined volume of the liquid,
   (2) bringing a second electrode into a closely spaced relationship with the first electrode, thereby contacting the sample with an area of the second electrode spaced apart from the first, wherein step (2) is conducted after step (1),
   (3) applying a potential between the electrodes while the electrodes are sufficiently closely spaced that reaction products formed at each electrode diffuse to the other electrode while the potential is applied, (4) measuring or estimating a value indicative of the change in current as a function of time and a value indicative of the steady state current, and (5) determining from said value, said current as a function of time, and said steady state current the concentration of reduced or oxidized form of the species in the liquid sample wherein at least one of the electrodes is in the form of a continuous strip.

2. A method according to claim 1 wherein at least one of the electrodes is preprinted with at least one reagent.

3. A method according to claim 1 wherein at least one electrode is covered with a layer which serves to define wells on the electrode surface.

4. Apparatus according to claim 1, further comprising a pipette for depositing a drop of a predetermined volume of sample on the first electrode.

5. The method according to claim 1, wherein the first electrode comprises a first metallized electrode layer, wherein the second electrode comprises a second metallized electrode layer, and wherein the first metallized electrode layer travels transversely of the second electrode layer.

6. The method according to claim 1, wherein the first electrode comprises a first metallized electrode layer, wherein the second electrode comprises a second metallized electrode layer, and wherein the first metallized electrode layer travels in a same direction as the second electrode layer.

7. An automatic analyzing apparatus comprising:

a first electrode, means for placing a predetermined volume of a liquid sample in contact with the first electrode, means for bringing a second electrode into a closely spaced relationship with the first electrode after a predetermined volume of a liquid sample has been brought in contact with the first electrode, thereby contacting the sample with the second electrode spaced from the first, means for applying a potential between the electrodes, and means for measuring the current as a function of time while the electrodes are in sufficiently close proximity that reaction products formed at one electrode diffuse to the other and achieve a steady state distribution wherein a volume intermediate the electrode surfaces when the current is measured is not contained by a cell.

8. Apparatus according to claim 7 wherein the first electrode further comprises a porous medium wherein the predetermined volume is immobilized.

9. Apparatus according to claim 7 wherein at least one of the electrodes is a palladium layer.

10. Apparatus according to claim 7 further comprising a pipette for depositing a predetermined volume of sample in contact on the first electrode.

11. Apparatus according to claim 7 further comprising means for depositing one or more reagents on one of the electrodes prior to placing the sample on the electrode.

12. Apparatus according to claim 7, wherein the first electrode further comprises a well defining layer, the well defining layer comprises an aperture, the aperture defining a well.

13. Apparatus according to claim 7, wherein the first electrode or the second electrode further comprises a predetermined quantity of a chemical reagent.

14. Apparatus according to claim 7, wherein at least one of the first electrode and the second electrode is in the form of a disposable probe.

15. Apparatus according to claim 7, wherein at least one of the first electrode and the second electrode is in the form of a retractable probe.

16. An automatic analyzing apparatus comprising:

a first electrode, means for placing a predetermined volume of a liquid sample in contact with the first electrode, means for bringing a second electrode into a closely spaced relationship with the first electrode after a predetermined volume of a liquid sample has been brought in contact with the first electrode, thereby contacting the sample with the second electrode spaced from the first, means for applying a potential between the electrodes, and means for measuring the current as a function of time while the electrodes are in sufficiently close proximity that reaction products formed at one electrode diffuse to the other and achieve a steady state distribution wherein at least one electrode is in the form of a continuous strip.

17. An automatic analyzing apparatus comprising:

a first electrode, means for placing a predetermined volume of a liquid sample in contact with the first electrode, means for bringing a second electrode into a closely spaced relationship with the first electrode after a predetermined volume of a liquid sample has been brought in contact with the first electrode, thereby contacting the sample with the second electrode spaced from the first, means for applying a potential between the electrodes, and means for measuring the current as a function of time while the electrodes are in sufficiently close proximity that reaction products formed at one electrode diffuse to the other and achieve a steady state distribution wherein at least one electrode is on a flexible backing.

18. An automatic analyzing apparatus comprising:

a first electrode, means for placing a predetermined volume of a liquid sample in contact with the first electrode, means for bringing a second electrode into a closely spaced relationship with the first electrode after a predetermined volume of a liquid sample has been brought in contact with the first electrode, thereby contacting the sample with the second electrode spaced from the first, means for applying a potential between the electrodes, and means for measuring the current as a function of time while the electrodes are in sufficiently close proximity that reaction products formed at one electrode diffuse to the other and achieve a steady state distribution wherein at least one of the first electrode and the second electrode is mounted on a carousel.

* * * * *